(12) United States Patent
Baplue et al.

(10) Patent No.: US 8,348,903 B2
(45) Date of Patent: Jan. 8, 2013

(54) DISPENSER CARTRIDGE FOR RADIOPHARMACEUTICALS

(75) Inventors: Frédéric Baplue, Liège (BE); Philippe Bekaert, Huy (BE); Jean-Luc Morelle, Liege (BE); Gauthier Philippart, Grand Rechain (BE)

(73) Assignee: Trasis S.A., Liege (BE)

( * ) Notice: Subject to any disclaimer, the term of this patent is extended or adjusted under 35 U.S.C. 154(b) by 1822 days.

(21) Appl. No.: 11/545,895

(22) Filed: Oct. 11, 2006

(65) Prior Publication Data

US 2008/0171999 A1 Jul. 17, 2008

(51) Int. Cl.
*A61M 5/32* (2006.01)
*A61M 5/00* (2006.01)

(52) U.S. Cl. ....................... 604/195; 604/232
(58) Field of Classification Search .................. 604/232, 604/199, 200, 201, 195
See application file for complete search history.

(56) References Cited

U.S. PATENT DOCUMENTS

| | | | |
|---|---|---|---|
| 3,021,942 A | 2/1962 | Hamilton | |
| 3,074,542 A | 1/1963 | Myerson et al. | |
| 4,048,997 A * | 9/1977 | Raghavachari et al. | 604/189 |
| 4,056,096 A | 11/1977 | Collica et al. | |
| 4,122,836 A | 10/1978 | Burnett | |
| 4,241,728 A * | 12/1980 | Mirell | 600/5 |
| 4,615,468 A | 10/1986 | Gay | |
| 4,781,697 A | 11/1988 | Slaughter | |
| 4,892,525 A | 1/1990 | Hermann, Jr. et al. | |
| 4,994,012 A | 2/1991 | Nakayama et al. | |
| 5,615,772 A | 4/1997 | Naganuma | |
| 5,693,028 A | 12/1997 | Shillington | |
| 5,716,317 A | 2/1998 | Okano et al. | |
| 5,807,343 A * | 9/1998 | Tucker et al. | 604/187 |
| 5,828,073 A | 10/1998 | Zhu et al. | |
| 5,918,443 A | 7/1999 | Phillips | |
| 5,925,029 A * | 7/1999 | Jansen et al. | 604/411 |
| 6,258,078 B1 * | 7/2001 | Thilly | 604/411 |
| 6,352,522 B1 * | 3/2002 | Kim et al. | 604/201 |
| 6,494,824 B1 | 12/2002 | Apple et al. | |
| 6,614,040 B1 | 9/2003 | Zens | |
| 6,722,499 B2 | 4/2004 | Reich | |
| 7,628,779 B2 * | 12/2009 | Aneas | 604/411 |
| 2002/0139088 A1 * | 10/2002 | Woodworth et al. | 53/426 |
| 2003/0144634 A1 * | 7/2003 | Langley et al. | 604/232 |
| 2004/0084340 A1 | 5/2004 | Morelle et al. | |

FOREIGN PATENT DOCUMENTS

EP 0 661 066 7/1995
JP 02 095380 7/1990

* cited by examiner

*Primary Examiner* — Nicholas Lucchesi
*Assistant Examiner* — Weng Lee
(74) *Attorney, Agent, or Firm* — Merchant & Gould P.C.

(57) ABSTRACT

A cartridge for radiopharmaceutical packaging includes a low UV-absorbing plastic barrel, closed at one end by a cap and at the other by a piston. A shoulder cooperates with the barrel in a double-level snap-on system with a cavity cooperating with an injection fitting sleeve to make a seal. At a first end the cap has a peel-off porous liner covering the cavity. Radial fins protrude inside the cavity, for screwing the injection fitting and second radial fins protrude outside of the cap to fix to a cartridge protection shield. A second end minimizes a shadow area of UV flash lamp sterilization and ensures clearance for inserting an injection spike. The second end has a reduced wall thickness pierced by the spike during set up for dispensing of the pharmaceutical. An external cylindrical zone at the second end ensures leak tightness between the cap and the barrel.

8 Claims, 6 Drawing Sheets

PRIOR ART

FIG.1A  FIG.1B

PRIOR ART

DISPENSER CARTRIDGE FOR RADIOPHARMACEUTICALS

FIELD OF THE INVENTION

The present invention is related to practices in nuclear medicine, and in particular to a device for preparing automatically radiopharmaceutical products suitable for injection.

BACKGROUND OF THE INVENTION

The development of nuclear medicine, in particular in the field of diagnosis by positron emission tomography (PET), makes it necessary to review the usual methods for producing, packaging and handling radiopharmaceutical substances intended for administration to patients.

Radiopharmaceutical substances are chemical compounds labeled with radioactive isotopes, intended for medical use. Problems of existing methods and equipment are mainly due to the increase in the use of isotopes whose radiation energy is relatively high, and to the fact that a higher level of automation is required due to the short half-life of said isotopes.

Dose fractionation systems are available on the market. They make it possible to dilute a base radiopharmaceutical product, to prepare the dilute solution in vials and to place these vials in a radiation shielding device for transportation. The vials are then delivered to the nuclear medicine departments of hospitals. Such devices are mainly used by radiopharmaceutical production companies.

Currently the doses are prepared either in "multi-dose" vials, such as penicillin crimped cap vials out of which the medical staff draws with a syringe the desired amount for a single patient (especially in Europe), or directly loaded as single doses and shipped in syringes (especially in the U.S.A.).

Figure 1A:
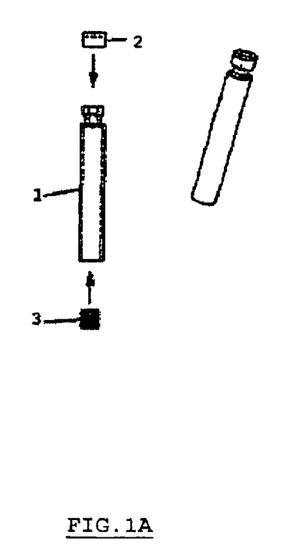
FIG. 1A to FIG. 1C, already mentioned, represent an overview of a device to be used in the automated preparation, packaging and handling of a radiopharmaceutical compound as known in current art.
Figure 1B:
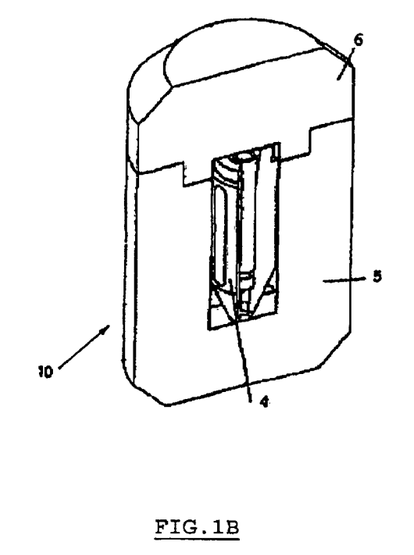
Figure 1C:
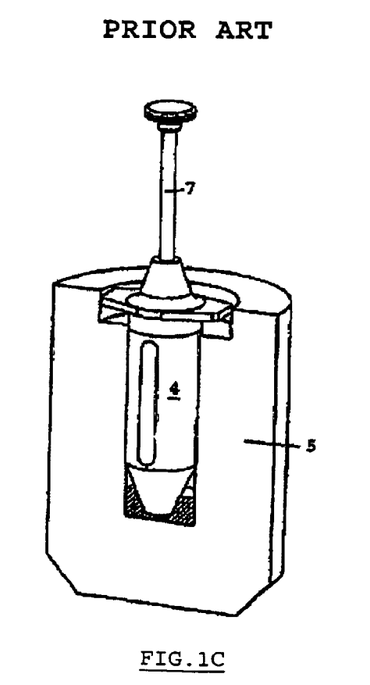

Problems related to the current art practice are described in U.S. Patent Application Publication No. US 2004/0084340 A1 (PCT No. PCT/BE02/00050). This document describes a device to be used in the automated preparation, packaging and further handling of an individual dose of a radiopharmaceutical compound, comprising the following set of elements (see FIGS. 1A, 1B and 1C):

- a cartridge 1 intended to contain said individual dose, provided at a first end with a closing element 2 and at a second end with a component serving as a piston 3;
- a radiation-shielding container 10 comprising an inner cylinder-like part 4 capable to enclose the sealed cartridge 1, and an outer cylinder-like part 5, serving as an additional shielding for transportation. The outer part, provided with a shielding lid 6, is capable to enclose the inner part;
- a plunger 7 to be fitted to the cartridge 1 at the time of an injection, while said cartridge is still inside said inner cylinder-like part 4 of the radiation shielding container 10, provided with a sliding rod capable to contact and move, i.e. push or pull said piston 3 of the cartridge 1.

An injection means can be fitted to the first end of the cartridge at the time of an injection, while the cartridge is still inside said inner cylinder-like part of the radiation shielding container. The closing element 2 is a septum, such as an elastomeric stopper and the injection means is capable to pierce this septum in a sterile manner and thus to enter in contact with the radiopharmaceutical compound.

AIM OF THE INVENTION

The present invention aims to provide a device specifically designed for the preparation of single patient radiopharmaceutical doses in nuclear medicine procedures, so that the exposure of the operators to radiation, either in the production facility or in the hospital, and the risk of bacteriological contamination of the contained pharmaceutical solution are both minimized.

The invention also aims at providing a device particularly suited for automated preparation procedures.

SUMMARY OF THE INVENTION

A first object of the present invention relates to a improved cartridge for the packaging of a pharmaceutical, and preferably a radiopharmaceutical, comprising a plastic barrel, preferably made of low UV-absorbing matter, closed at one end by a cap and at the other end by a piston. Said cap is provided at least partly with:

- a shoulder cooperating with the barrel in a double-level snap-on system;
- a cavity to cooperate with an elastomeric protection sleeve of an injection means fitting, to make a seal, said cap being terminated at a first end by a peel-off porous liner covering said cavity;
- a first plurality of radial fins protruding inside said cavity, for screwing the injection means fitting and with a second plurality of radial fins protruding on the outside of the cap to ensure fixation of the cap into a cartridge protection shield;
- a second end opposite to the first end, shaped so that to minimize a shadow area in the case of UV flash lamp sterilization and to ensure sufficient clearance for inserting a spike of the injection means, said second end having a reduced wall thickness for acting as a septum intended to be pierced by said spike at the time of setting up for dispensing the pharmaceutical to a patient;
- an external cylindrical zone at this second end to ensure leak tightness between the cap and the barrel.

Preferably, the injection means fitting consists in a spike fitting of the type sample luer adapter, such as used for sampling blood.

In a more detailed feature of the invention, the peel-off porous liner is made of a material selected from the group consisting of paper and Tyvex®.

According to a preferred embodiment, the cartridge barrel is provided at least partly with:

- a first neck with staged shoulders or bosses for cooperating with the shoulder of the cap in a double-level snap-on system;
- a second neck with internal axial flutes for evacuating air when closing the barrel with the cap;
- a third neck with a perfectly cylindrical leak tightness area;
- a barrel body shaped so that to allow suitable exposure to light throughout a wetted area, said body being made of a material highly transparent to UV light;
- a rest area with a slightly increased internal diameter at the opposite side of said necks, for fitting the piston in the barrel.

In another more detailed feature of the invention, the shoulder of the cap and the first neck with staged shoulders of the barrel are configured so that said double-level snap-on system comprises a first shallowest snap position, reversible and open to air circulation to maintain the cap on the barrel and a second deepest snap position, leak-tight and irreversible for finally sealing the barrel after filling.

In another more detailed feature of the invention the barrel body is made of COP/COC plastic.

According to another preferred embodiment of the invention, the piston is provided at least partly with:

a reversible fixing system for connecting and disconnecting a piston rod to the piston;

a guiding system allowing to push on and guide the piston;

an end shaped so that to avoid any shadow to sterilization light flashes in the wetted area and to ensure sufficient clearance for the tip of the spike of the injection means.

Another object of the invention relates to an injection instrument intended to be reversibly snapped on the piston of the aforementioned cartridge, so that to form a temporary syringe plunger, comprising a piston rod itself comprising a central rod and a tube surrounding the latter, said central rod being ended with a profiled tip capable to be inserted in a corresponding profiled cavity in the piston, said tube being capable to slide lengthwise along the central rod and to maintain an outer rubber-like lip of the piston cavity closed onto the tip of the central rod, so that it fastens the piston onto the injection tool.

Preferably, when the tube is retrieved, the rubber-like lip of the piston cavity is free to bend, so that to release the tip of the central rod.

In a more detailed preferred embodiment, the central rod and its surrounding sleeve extend at the end opposite to the piston to a push-button including an actuation mechanism, so that the relative displacement between central rod and outer tube either fastens or releases the injection tool from the piston.

Another object of the invention relates to a machine for filling the above mentioned cartridges with a pharmaceutical.

Another object of the invention relates to a device to be used in the automated preparation, packaging and further handling of a radiopharmaceutical solution, comprising the following set of elements:

a cartridge, as described above, intended to contain said individual dose of the pharmaceutical solution;

a radiation-shielding container comprising an inner cylinder-like part capable to enclose said cartridge, and an outer part, serving as an additional shielding for transportation, said outer part being capable to enclose said inner part, said outer part being provided with a shielding lid;

an injection instrument, as described above, to be fitted onto the cylinder-like part at the time of an injection, while said inner cylinder-like part is still inside the radiation shielding container;

an injection means to be fitted to the cap of the cartridge at the time of injection, while said cartridge is still inside said inner cylinder-like part of the radiation shielding container, said injection means being capable to pierce the cap septum in a sterile manner and to enter in contact with said pharmaceutical compound.

BRIEF DESCRIPTION OF THE DRAWINGS

FIG. 4A and FIG. 4B represent cross-sectional views of the cap coupled to the cartridge barrel in the first and second snap-on positions respectively. In FIG. 4B, the SLA has been shown inserted leak-tightly in the cap with its spike piercing the septum.

DESCRIPTION OF A PREFERRED EMBODIMENT OF THE INVENTION

Cartridge Assembly: Overview

Figure 2:
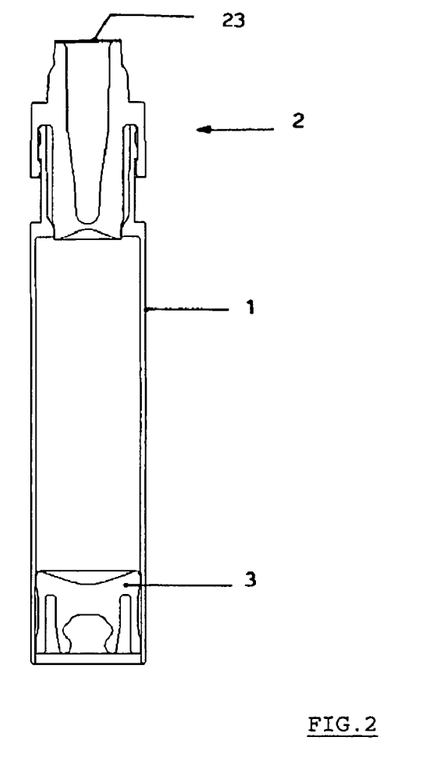
FIG. 2 represents a cross-sectional complete view of the 3-parts cartridge according to the invention.

As shown on FIG. 2, a specific cartridge has been specifically developed for the packaging of radiopharmaceuticals. It consists in a plastic barrel 1, essentially transparent to visible and UV light, closed at one end by a cap 2 and at the other by a piston 3. The cartridge has specific and original features to:

facilitate an accurate, fast and aseptic automated handling and filling of the cartridge;

allow fast sterilization of the cartridge content using intense UV light flashes;

facilitate administration of its content to the patient in safe aseptic conditions.

Cap

Figure 3:
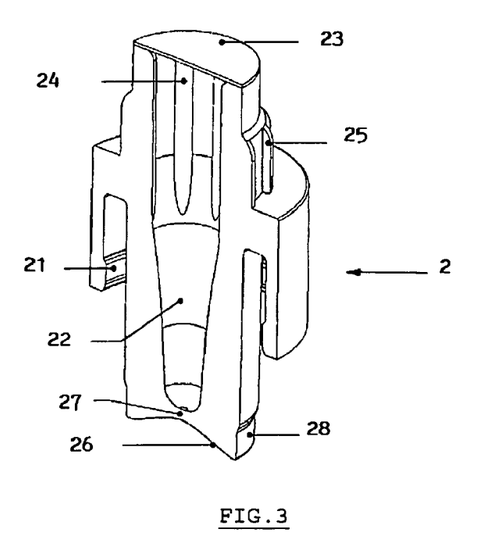
FIG. 3 represents a cutaway view of the cartridge cap with a porous liner.

As shown on FIG. 3, the cap 2 is designed to easily accommodate sample luer adapters (SLA), in particular to make a seal using the rubber sleeve protecting the spike of the SLA. Such SLA, well-known by the one skilled in the art, are originally designed for the collection of blood samples and are available from several major suppliers of components for medical use. An internally-oriented shoulder 21 on the cap allows it to fit firmly on the cartridge 1. The cap and the cartridge (see details below) cooperate in a double-level snap system, simplifying the handling during filling and packing of the cartridges.

Thus the two-levels snapping system of the cap onto a dedicated cartridge allows the cap 2 to be packed with said cartridge barrel 1 to simplify the automation of the filling process. As shown on FIG. 4A, the first, shallowest, snap position 13 is reversible. It does not seal the cartridge and is purposely open to the circulation of air. It maintains cap 2 on the cartridge barrel 1. In this position, the cap can still be removed from the cartridge. The caps are fitted on the empty cartridges in this position as initially supplied to the radiopharmacies, prior to filling. As shown on FIG. 4B, the second, deepest, snap position 14 is final, irreversible and seals the cartridge in a closed position after being filled. The outer side of cap 2, defined as the side not in contact with the injection fluid, has a specially designed cavity 22 into which a spike fitting such as a SLA, usually used for sampling blood, can be screwed. The dimensions of the cavity 22 in the cap can accommodate several models of SLA. The cavity is protected from dust and germs by a peel-off porous liner 23 (for example made of paper or Tyvex®).

Figure 4A:
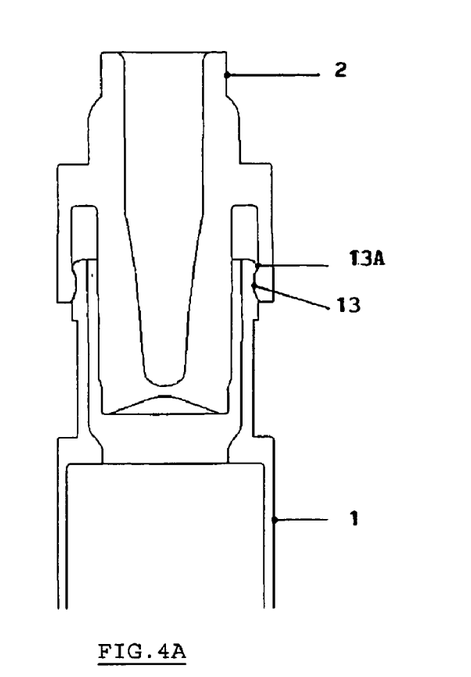
Figure 4B:
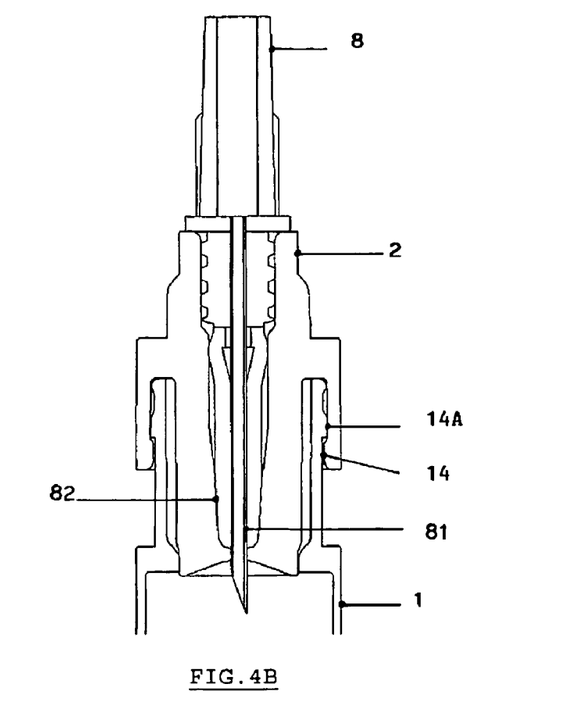

According to the invention, specific features of cap 2 are:

a snap-on shoulder 21 for a double-level positioning of cap 2 onto barrel 1, allowing a storage of the caps together with the cartridges to simplify the automation of the filling process;

the use of the rubber protection sleeve 82 of the sample luer adapter (SLA) 8 as a seal (FIG. 4B);

a peel-off porous liner 23 covering the cavity in which the SLA will be inserted, to ensure sterility;

a set of radial fins 24 protruding inside the cavity, in which the SLA can be screwed. This system can accommodate different thread sizes from different SLA models such as Luer Adapter Cat. No. 26537 from Excel, Monoject Ref. Code 8881225257 from Kendall (Tyco), Venoject Ref.

XX-MN2000 or TXX-MN2000T from Terumo®, Vacutainer® Systems Luer Adaptor Ref. 367300 from Becton Dickinson a set of radial fins 25 protruding on the outside of the cap to ensure that the cap is well fixed into the cartridge shield 4 (see above);

a specially shaped end 26 of the cap on the cartridge side, for minimizing the shadow area to allow flash lamp sterilization and for ensuring sufficient clearance when inserting the spike into the septum a reduced wall thickness 27 at the bottom of the cap, acting as a septum that is intended to be pierced by the spike 81 of the SLA when setting up the system for dispensing the product to the patient;

a well-finished cylindrical zone 28 to ensure leak tightness between the cap and the cartridge. Its position ensures that the pharmaceutical cannot go in a zone that cannot be sterilized.

Cartridge Barrel

Figure 5:
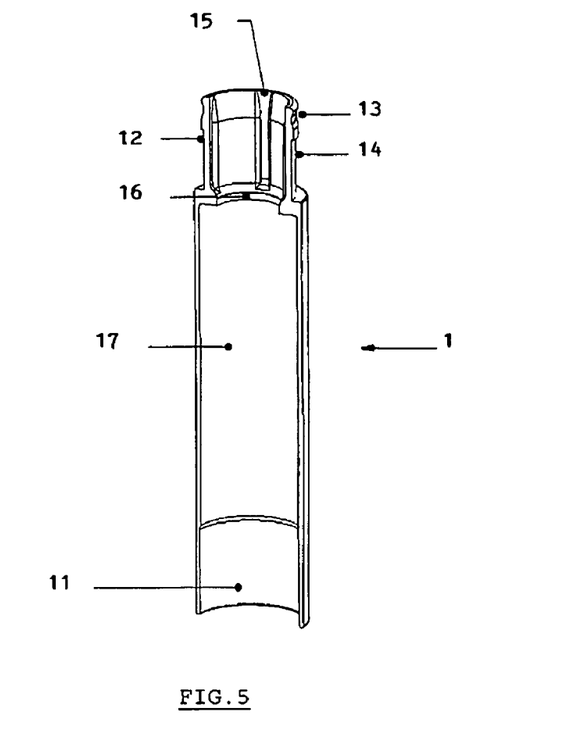
FIG. 5 represents a cutaway view of the cartridge barrel.

As shown on FIG. 5, the cartridge barrel 1 is a cylindrical 3 mL container open at both ends. A cap 2 is fixed at one end and a piston 3 closes the other end. The neck on the cap 2 side of the cartridge is profiled in such way to allow the double level snap-on fixture of the cap (FIGS. 4A and 4B). The cartridge 1 is made of a low UV absorbing plastic, such as Cyclic Olefin Polymer (COP) or Cyclic Olefin Copolymer (COC), to allow flash lamp sterilization of the product inside the cartridge.

The cartridge barrel 1 has an increased internal diameter at the end opposite to the cap, which serves as a rest position 11 for the piston 3. The stress on the piston's seal line area is then reduced to prevent swelling during storage.

Specific features of the cartridge barrel 1 are:
a neck 12 with staged shoulders or bosses 13A, 14A, configured to allow a double position snapping of cap 2, one position loose and reversible 13, while the other position 14 is final and leak tight (FIGS. 4A, 4B and 5)

a neck with internal axial (vertical) flutes 15 to evacuate air when closing the cartridge with the cap;

a neck with a perfectly cylindrical leak tightness area 16. Its position ensures that the pharmaceutical cannot get into a zone that cannot be sterilized;

a suitably shaped body 17 allowing a good exposure to light throughout the wetted area;

a high transparency to UV light, using high transmission COC, COP or other high UV transparent plastic;

a rest area 11 with an increased internal diameter of the cartridge for accommodating the piston at the opposite side of said necks.

Piston

Figure 6:
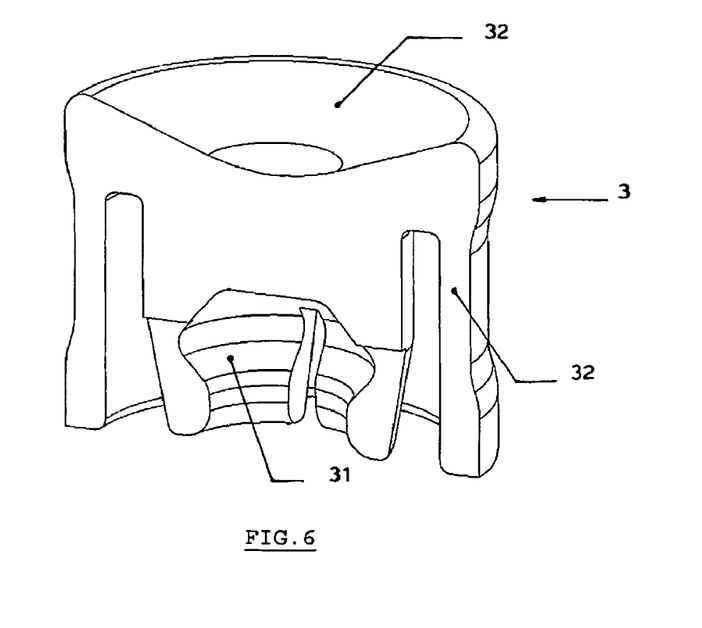
FIG. 6 represents a cutaway view of the piston.

As shown on FIG. 6, the piston 3 is also intended to be located on the cartridge barrel 1. It is designed with a clamping system allowing reversible fixture to a removable piston rod (see below). The piston 3 can then be pushed and pulled, allowing not only to empty the cartridge, but also to aspirate a fluid to rinse the cartridge and transfer the dose without loss to the patient. After administration of the product, the piston rod can be released from the piston by means of the piston rod's clamping mechanism.

Specific features of the piston 3 are:
a fixing system 31 allowing to connect and disconnect a piston rod to the piston 3;

an external lip 32 allowing to push on and to guide the piston 3;

a specially shaped side 33 to avoid any shadow to sterilization light flashes in the wetted area and to ensure sufficient clearance for the tip of the spike of the injection means.

Packing Box

The cartridge assemblies, consisting each of a barrel 1 with its piston 3 and its cap 2 snapped in the storage position and peel-off seal 23, are packed in boxes having a capacity convenient for the use (a typical model contains 295 cartridges). The boxes are closed by a lid which automatically slides open (or closed) when placed (or removed) on (from) the dispensing machine, preventing the cartridges from falling out during any handling operation. This also prevents the cartridges from ever being touched by operators throughout the process. A radiofrequency identification (RFID) tag on the cartridge box allows knowing at any time the number of cartridges remaining in the box.

Specific features are (not shown):
a sliding lid that opens when placed and closes when removed;

a box that behaves as a cartridge feed hopper when placed on the dedicated filling machine.

Injection Instrument

Figure 7A:
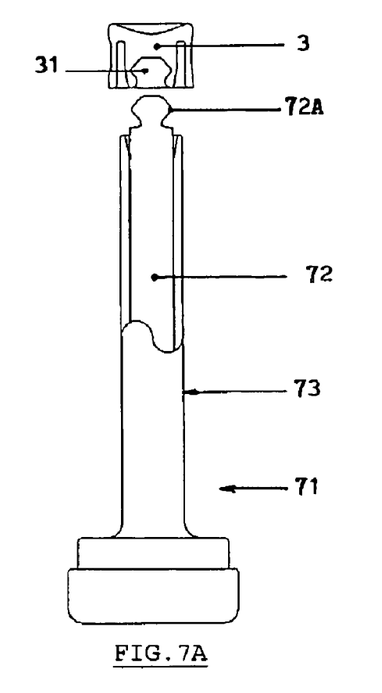
FIG. 7A to FIG. 7C represent different cross-sectional views of the injection tool according to the invention, in relative position about the piston.
Figure 7B:
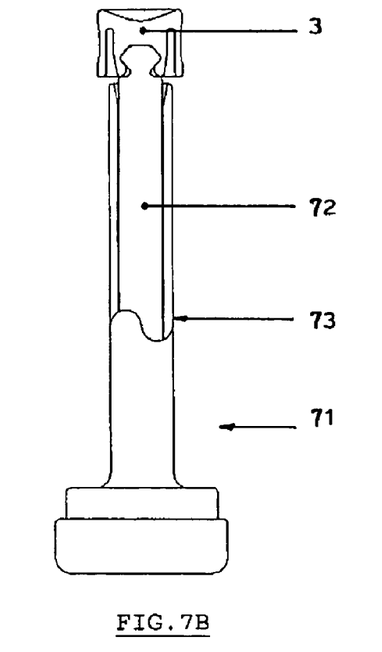
Figure 7C:
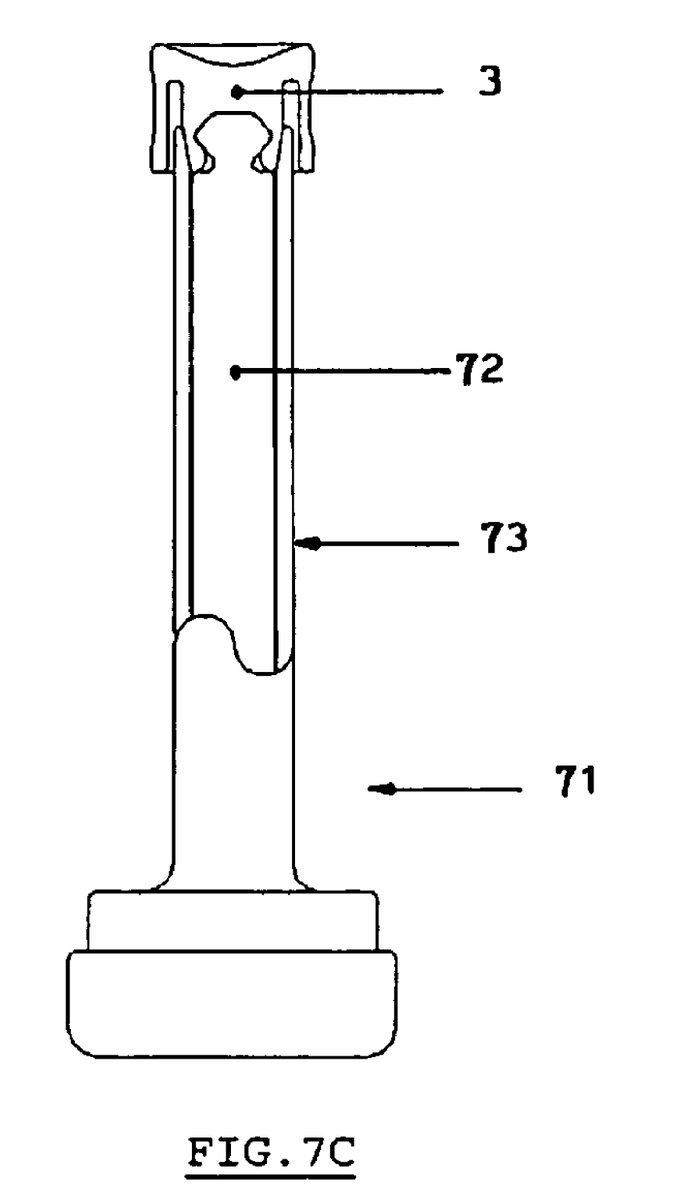

As shown on FIG. 7A to 7C, the injection instrument comprises a specifically designed piston rod 71 allowing the reversible snapping of the rod on the piston. When fixed together, the piston and the piston rod form a temporary syringe plunger. This plunger can be pushed in and pulled out, allowing flow in and out of the cartridge.

The piston rod 71 consists in a central rod 72 ended with a profiled tip 72A that can be inserted in the corresponding profiled cavity 31 in the piston 3, surrounded with a tube 73 that can slide lengthwise along the central rod 72 and maintain the outer lip of the piston cavity 31 closed onto the tip 72A of the central rod 72 (FIG. 7C).

When the tube 73 is pulled out, the rubber-like lip of the piston cavity can bend, which permits to release the tip 72A away from the central rod 72 (FIG. 7B).

The central rod 72 and surrounding tube 73 extend at the end opposite to the piston 3 to a push button including the actuation mechanism (not shown), allowing the relative displacement between central rod and outer tube to either fasten or release the injection tool to or from the piston 3.

Specific features of the injection instrument are:
a central rod 72 ended with a profiled head 72A adapted to the shape of corresponding cavity 31 in the piston 3 (FIG. 7A);

a sliding tube 73 around the central rod that holds the lip of the piston in place to fasten the piston onto the injection instrument (FIG. 7C).

The invention claimed is:

1. A cartridge for the packaging of a pharmaceutical comprising a plastic barrel, closed at one end by a cap and at the other end by a piston, wherein said cap is provided at least partly with:

a shoulder cooperating with the barrel in a double-level snap-on system;

a cavity configured to accommodate an elastomeric protection sleeve of injection means fitting, to make a seal, said cap being terminated at a first end by a peel-off porous liner covering said cavity;

a first plurality of radial fins protruding inside said cavity, for screwing the injection means fitting and with a second plurality of radial fins protruding on the outside of the cap to ensure fixation of the cap into a cartridge protection shield;

a second end opposite to the first end and facing the barrel, shaped so to minimize a shadow area in the case of UV flash lamp sterilization and to ensure sufficient clearance for inserting a spike of the injection means, said second end being closed and having a reduced wall thickness for acting as a septum to be pierced by said spike at the time of setting up for dispensing the pharmaceutical to a patient;

an external cylindrical zone at the second end to ensure leak tightness between the cap and the surrounding barrel;

the barrel being provided at least partly with:
- a first neck with staged shoulders or bosses for cooperating with the shoulder of the cap in a double-level snap-on system;
- a second neck with internal axial flutes for evacuating air when closing the barrel with the cap;
- a third neck with a perfectly cylindrical leak tightness area;
- a barrel body shaped to allow suitable exposure to light throughout a wetted area, said body being made of a material transparent to UV light,
- a rest area with a slightly increased internal diameter at the opposite side of said necks, for fitting the piston in the barrel.

2. The cartridge according to claim 1, wherein the pharmaceutical is a radiopharmaceutical.

3. The cartridge according to claim 1, wherein the plastic barrel is made of a low UV-absorbing plastic.

4. The cartridge according to claim 1, wherein the injection means fitting comprises a spike fitting of the type sample luer adapter, such as used for sampling blood.

5. The cartridge according to claim 1, wherein the peel-off porous liner is made of a material selected from the group consisting of paper and synthetic material made of woven high-density polyethylene fibers.

6. The cartridge according to claim 1, wherein the shoulder of the cap and first neck with staged shoulders of the barrel are configured so that said double-level snap-on system comprises a first shallow snap position, reversible and open to air circulation to maintain the cap on the barrel and a second deep snap position, leak-tight, irreversible for finally sealing the barrel after filling.

7. The cartridge according to claim 1, wherein the barrel body is made of COP/COC plastic.

8. The cartridge according to claim 1, wherein the piston is provided at least partly with:
- a reversible fixing system for connecting and disconnecting a piston rod to the piston;
- a guiding system providing for pushing on and guiding the piston;
- an end shaped to avoid any shadow to sterilization light flashes in the wetted area and to ensure sufficient clearance for the tip of the spike of the injection means.

* * * * *